United States Patent
Fankhauser et al.

(10) Patent No.: US 9,486,887 B2
(45) Date of Patent: Nov. 8, 2016

(54) TOOL CHUCKING DEVICE

(75) Inventors: Marcel Fankhauser, Bern (CH);
Bruno Luescher, Zofingen (CH);
Szabolcs Gyori,
Leinfelden-Echterdingen (DE)

(73) Assignee: Robert Bosch GmbH, Stuttgart (DE)

( * ) Notice: Subject to any disclaimer, the term of this patent is extended or adjusted under 35 U.S.C. 154(b) by 339 days.

(21) Appl. No.: 13/981,512

(22) PCT Filed: Dec. 27, 2011

(86) PCT No.: PCT/EP2011/074105
§ 371 (c)(1),
(2), (4) Date: Dec. 9, 2013

(87) PCT Pub. No.: WO2012/100893
PCT Pub. Date: Aug. 2, 2012

(65) Prior Publication Data
US 2014/0110908 A1    Apr. 24, 2014

(30) Foreign Application Priority Data
Jan. 25, 2011    (DE) .......................... 10 2011 003 103

(51) Int. Cl.
*B23B 31/10*    (2006.01)
*B23Q 3/12*    (2006.01)
*A61B 17/14*    (2006.01)
(Continued)

(52) U.S. Cl.
CPC ................. *B23Q 3/12* (2013.01); *A61B 17/14* (2013.01); *A61B 17/148* (2013.01); *B23D 51/10* (2013.01); *B27B 5/30* (2013.01); *B27B 19/006* (2013.01); *B24B 23/022* (2013.01); *B24B 45/00* (2013.01); *B24B 45/006* (2013.01); *B27B 5/32* (2013.01); *Y10T 279/33* (2015.01)

(58) Field of Classification Search
CPC ... B24B 45/006; B24B 45/00; B24B 23/022; B23B 45/003; B27B 5/32; Y10T 279/33
See application file for complete search history.

(56) References Cited

U.S. PATENT DOCUMENTS 1,705,205 A    3/1929    Reams
5,158,331 A *  10/1992   Wesselski et al. .............. 294/94
(Continued)

FOREIGN PATENT DOCUMENTS

CH    563 847 A5    7/1975
CN    1805717 A     7/2006
(Continued)

OTHER PUBLICATIONS

International Search Report corresponding to PCT Application No. PCT/EP2011/074105, mailed Feb. 20, 2012 (German and English language document) (7 pages).

*Primary Examiner* — Eric A Gates
*Assistant Examiner* — Paul M Janeski
(74) *Attorney, Agent, or Firm* — Maginot, Moore & Beck LLP (57) ABSTRACT

A tool chucking device, especially an oscillation tool chucking device, includes at least one chucking unit which has at least one pin-type chucking element for clamping a treatment tool in an axial direction and at least one grip head arranged on the chucking element. The tool chucking device further includes at least one movement conversion unit which is designed to displace at least the grip head at least substantially along the axial direction into at least one direction different from the axial direction depending on the movement of the chucking element.

14 Claims, 4 Drawing Sheets

(51) Int. Cl.
    *B23D 51/10*    (2006.01)
    *B27B 5/30*    (2006.01)
    *B27B 19/00*    (2006.01)
    *B24B 45/00*    (2006.01)
    *B27B 5/32*    (2006.01)
    *B24B 23/02*    (2006.01)

(56) References Cited

U.S. PATENT DOCUMENTS

2005/0192585 A1    9/2005    Simmons
2009/0197514 A1*    8/2009    Peisert .................. B23Q 5/027
                                                            451/356
2012/0013081 A1*    1/2012    Craig et al. .................. 279/46.1

FOREIGN PATENT DOCUMENTS

| | | |
|---|---|---|
| CN | 101678483 A | 3/2010 |
| EP | 0 776 634 A2 | 6/1997 |
| EP | 1 752 256 A1 | 2/2007 |
| GB | 2 285 011 A | 6/1995 |
| RU | 2 082 593 C1 | 6/1997 |
| SU | 1 727 995 A1 | 4/1992 |
| WO | 95/13020 A1 | 5/1995 |

* cited by examiner

TOOL CHUCKING DEVICE

This application is a 35 U.S.C. §371 National Stage Application of PCT/EP2011/074105, filed on Dec. 27, 2011, which claims the benefit of priority to Ser. No. DE 10 2011 003 103.0, filed on Jan. 25, 2011 in Germany, the disclosures of which are incorporated herein by reference in their entirety.

BACKGROUND

There are already known tool clamping devices, in particular oscillating-tool clamping devices, that have a clamping unit. The clamping unit in these cases has a pin-shaped clamping element for chucking a working tool in an axial direction, and has a clamping head disposed on the clamping element.

SUMMARY

The disclosure is based on a tool clamping device, in particular an oscillating-tool clamping device, comprising at least one clamping unit that has at least one pin-shaped clamping element for chucking a working tool in an axial direction, and has at least one clamping head disposed on the clamping element.

It is proposed that the tool clamping device has at least one motion conversion unit, which is provided to move at least the clamping head, in dependence on a motion of the clamping element at least substantially along the axial direction, in at least one direction differing from the axial direction. In this context, the term "provided" is to be defined as specially equipped and/or specially configured. A "clamping unit" is to be understood here to mean, in particular, a unit that secures a working tool along the axial direction by means of a positive closure and/or by means of a non-positive closure, in particular on a tool receiver of a portable power tool. Preferably, when the clamping unit is in a clamping mode, a clamping force acts upon the working tool, along the axial direction. A "pin-shaped clamping element" is to be understood here to mean, in particular, a clamping element that, when in a mounted state, has a longitudinal extent, along the axial direction, that is greater than a transverse extent of the clamping element along a direction running perpendicularly in relation to the axial direction. In particular, the longitudinal extent is more than twice as great as the transverse extent of the clamping element, preferably more than four times as great, and particularly preferably more than six times as great. Preferably, the pin-shaped clamping element is realized at least partially as a hollow body. Particularly preferably, the clamping element has at least two partial regions, realized as limbs, which are disposed at a distance apart, relative to each other, at least partially, along a direction running at least substantially perpendicularly in relation to the axial direction. Preferably, the clamping element is disposed in a captive manner in a hollow shaft of the portable power tool. The term "axial direction" is intended here to define, in particular, a direction that preferably runs at least substantially parallelwise in relation to a swivel axis and/or a rotation axis of a drive shaft and/or spindle of a portable power tool that is provided to drive the working tool. "Substantially parallel" is to be understood here to mean, in particular, an alignment of a direction relative to a reference direction, in particular in one plane, the direction deviating from the reference direction by, in particular, less than 8°, advantageously less than 5°, and particularly advantageously less than 2°.

A "clamping head" is to be understood here to mean, in particular, an element having at least one clamping face that, for the purpose of chucking the working tool in the axial direction, bears against at least a partial surface of the working tool and acts with a clamping force upon the working tool along the axial direction. The term "motion conversion unit" is intended here to define, in particular, a unit comprising a mechanism by means of which a motion of a first element, in particular a translational motion of the first element, can be converted into a motion of a further element, in particular into a swivel motion and/or translational motion of the further element. Preferably, a translational motion of the clamping element is converted into a swivel motion and/or into a translational motion of the clamping head by means of the motion conversion unit. Particularly preferably, the clamping head is moved, by means of the motion conversion unit, at least substantially along a main motion component that runs at least substantially perpendicularly in relation to the axial direction. The expression "substantially perpendicularly" is intended here to define, in particular, an alignment of a direction relative to a reference direction, the direction and the reference direction, in particular as viewed in one plane, enclosing an angle of 90°, and the angle having a maximum deviation of, in particular, less than 8°, advantageously less than 5°, and particularly advantageously less than 2°. "Substantially along" is to be understood here to mean, in particular, a course of a direction along a reference direction, the direction deviating from the reference direction by, in particular, less than 8°, advantageously less than 5°, and particularly advantageously less than 2°. The design of the tool clamping device according to the disclosure makes it possible, advantageously, to achieve a clamping operation that is easy to perform. Further, through simple design means, it is possible to achieve chucking of the working tool on a tool receiver of the portable power tool, in particular a portable power tool having a spindle that can be driven in an oscillatory manner.

Further, it is proposed that the motion conversion unit has at least one motion conversion element, which is provided to move the clamping head in at least one direction differing from the axial direction, for the purpose of achieving an axial overlap of the clamping head and the working tool, at least when the clamping unit is in a clamping mode. A "clamping mode" is to be understood here to mean, in particular, a state of the clamping unit in which the working tool has been secured by means of the clamping element and/or the clamping head. In particular, in the clamping mode, the working tool is secured to a tool receiver of a portable power tool by means of the clamping unit, along the axial direction and/or along the radial direction, for the purpose of performing work on workpieces. Particularly preferably in this case, a clamping force is applied to the working tool along the axial direction. A "radial direction" is intended here to mean, in particular, a direction running at least substantially perpendicularly in relation to the axial direction. Preferably, the motion conversion element is realized such that it is separate from the clamping element and/or the clamping head. The expression "axial overlap" is intended here to define, in particular, an overlap, in particular of partial regions, of at least two components along the axial direction; in particular, a straight line intersects the two components along the axial direction. Preferably, when in the clamping mode, at least one clamping face of the clamping head overlaps at least one partial region of the working tool along the axial direction. Particularly preferably, when the clamping head is in a mounted state, the overlap can be temporarily removed, in particular for the purpose of changing the working tool and/or for the purpose of altering a position, in particular altering an angular position, of the working tool. Advantageously, it is possible to achieve chucking and/or release of the working tool without the use of tools. Advantageously, therefore, it is possible to dispense with an additional tool for chucking and/or release operations. Moreover, the working tool can be mounted and/or chucked on the tool receiver of the portable power tool without removal and/or demounting of the clamping element.

Advantageously, the motion conversion element is realized as stud. A "stud" is to be understood here to mean, in particular, an element having a longitudinal extent greater than a transverse extent that runs perpendicularly in relation to the longitudinal extent. Preferably, the stud is realized in the form of a cylinder. Particularly preferably, the stud is realized so as to be rotationally symmetrical about at least one axis. Preferably, the stud is composed of a solid material. It is also conceivable, however, for the motion conversion element to be of a different design, considered appropriate by persons skilled in the art. A motion conversion element can be achieved through simple design means. Moreover, particularly advantageously, in particular in the case of the stud being designed as a cylindrical stud, at least a partial region of the clamping head can slide on the motion conversion element in the case of a motion of the clamping head, as a result of a motion of the clamping element. Advantageously, it is possible to achieve a tool clamping device according to the disclosure that is sparing of material. Advantageously, therefore, it is possible to achieve a long service life of the tool clamping device according to the disclosure.

Preferably, the clamping head is disposed in a resilient manner on the clamping element. The expression "disposed in a resilient manner" is intended here to define, in particular, a non-jointed, spring-elastic coupling of an element to a further element, a relative motion of the elements being possible, without a joint and as a result of an elastic deflection of the elements relative to each other. Preferably, the resilient disposition is realized through special material properties and/or a special geometry of the clamping head and of the clamping element. In particular, the clamping head can be deflected, relative to the clamping element, by more than 1 mm, preferably more than 2 mm, and particularly preferably more than 5 mm. Advantageously, simple design means make it possible for the clamping head to be movable relative to the clamping element.

In addition, it is proposed that the motion conversion unit has at least one cam member, in which the motion conversion element engages, at least partially. A "cam member" is to be understood here to mean, in particular, an element of a cam mechanism. The term "cam mechanism" is intended here to define, in particular, a mechanism that, as a result of a motion of the cam member and as a result of acting in combination with the motion conversion element, operates a component that, as a result, executes a motion defined by the combined action of the cam member and the motion conversion element. A motion of one element can be converted into a motion of a further element through simple design means. Advantageously, therefore, it is possible to achieve a tool clamping device that is easy to operate.

Preferably, the cam member is disposed on the clamping element. Particularly preferably, the cam member is realized as a slot. The slot is constituted, in particular, by a material cut-out in the clamping element. Preferably, in comparison with a region of the clamping element that adjoins the cam member, the cam member is of a lesser material thickness, in particular a material thickness of 0 mm. It is also conceivable, however, for at least two ribs to be disposed on an outer face of the clamping element, the motion conversion element engaging, at least partially, in the ribs. In particular, in this case, the at least two ribs can extend, starting from the outer face, at least substantially perpendicularly in a direction oriented away from the clamping element, such that the at least two ribs can constitute a guide for the motion conversion element. Other designs for constituting a cam member that are considered appropriate by persons skilled in the art are likewise conceivable. The motion conversion element preferably extends through the cam member, in particular along a direction running at least substantially perpendicularly in relation to the axial direction. The term "extend through" is to be understood here to mean, in particular, that the motion conversion element has a main extent along a radial direction, which runs at least substantially perpendicularly in relation to the axial direction and which is greater than an extent of the cam member along the radial direction running at least substantially perpendicularly in relation to the axial direction. Advantageously, a saving of structural space can be achieved. As a consequence, advantageously, a compact tool clamping device can be achieved.

Further, it is proposed that at least the clamping head has at least two partial regions that are movable relative to each other. Preferably, the two partial regions are movable relative to each other because of an elastic material property and/or a special geometry of the clamping head. Preferably, the two partial regions are movable relative to each other as a result of the clamping head being resiliently coupled to the clamping element. In an alternative design of the tool clamping device according to the disclosure, the clamping element likewise has two partial regions that are movable in relation to each other. In this case, the partial regions of the clamping element are mounted such that they can be swiveled relative to each other. Particularly preferably in this case, a partial region of the clamping head is realized, respectively, so as to be integral with a partial region of the clamping element. Advantageously, symmetrical chucking of the working tool can be achieved, in particular on a tool receiver of a portable power tool.

Advantageously, the motion conversion unit is realized as an expansion unit, which is provided to move at least two partial regions of the clamping head, which are movable relative to each other, in oppositely oriented directions relative to each other, in at least one operating mode of the clamping unit. An "expansion unit" is to be understood here to mean, in particular, a unit provided to move at least two partial regions of a component relative to each other. Preferably, the partial regions of the clamping head and/or of the clamping element are moved along a main motion component, which runs at least substantially perpendicularly in relation to the axial direction. Through simple design means, it is possible to achieve a motion of two partial regions of the clamping head and/or of the clamping element.

Preferably, the clamping head is realized so as to be integral with the clamping element. "Integral with" is to be understood here to mean, in particular, connected at least in a materially bonded manner, for example by a welding process, an adhesive bonding process, an injection process and/or by another process considered appropriate by persons skilled in the art, and/or, advantageously, formed in one piece, such as, for example, by being produced from a casting and/or by being produced in a single- or multi-component injection process and, advantageously, from a single blank. Advantageously, saving in assembly work can be achieved.

Further, the disclosure is based on a portable power tool, in particular a portable power tool having a spindle that can be driven in an oscillatory manner, having at least one tool clamping device according to the disclosure. A "portable power tool" is to be understood here to be, in particular, a power tool for working of workpieces, in particular a handheld power tool, that can be transported by an operator without a transport machine. The portable power tool has, in particular, a mass of less than 40 kg, preferably less than 10 kg, and particularly preferably less than 5 kg. Advantageously, it is possible to achieve a high degree of operating comfort for an operator of the power tool.

The tool clamping device according to the disclosure is not intended in this case to be limited to the application and embodiment described above. In particular, the tool clamping device according to the disclosure can have individual elements, components and units that differ in number from a number stated herein, in order to fulfill a principle of function described herein.

BRIEF DESCRIPTION OF THE DRAWINGS

Further advantages are given by the following description of the drawing. The drawing shows exemplary embodiments of the disclosure. The drawing, the description and the claims contain numerous features in combination. Persons skilled in the art will also expediently consider the features individually and combine them to create appropriate further combinations.

In the drawing.

DETAILED DESCRIPTION

Figure 1:
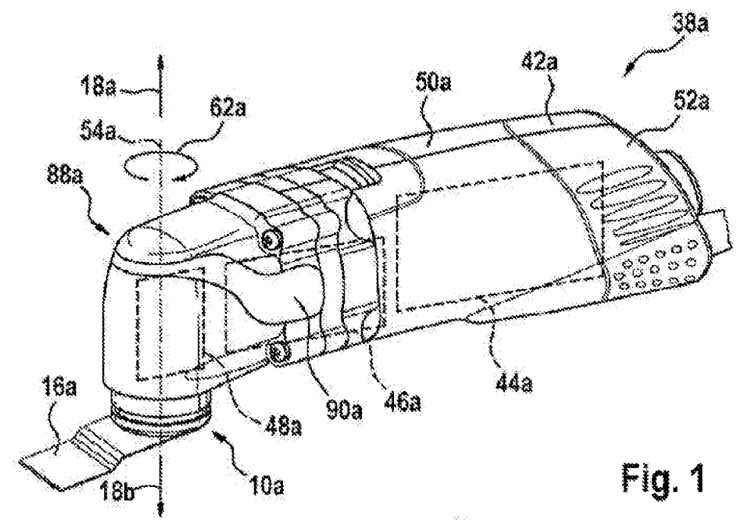
FIG. 1 shows a power tool according to the disclosure having a tool clamping device according to the disclosure, in a schematic representation.
Figure 2:
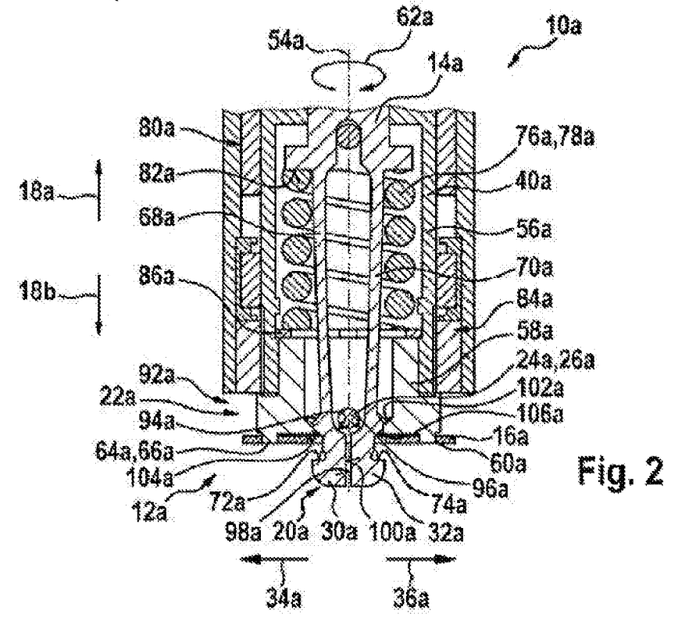
FIG. 2 shows a detail view of the tool clamping device according to the disclosure, in a tool changing mode of a clamping unit of the tool clamping device according to the disclosure, in a schematic representation.

FIG. 1 shows an electrically operated, portable power tool 38a, having a tool clamping device 10a. The portable power tool 38a comprises a power-tool housing 42a, which encloses an electric motor unit 44a, a transmission unit 46a and an output unit 48a of the portable power tool 38a. The power tool housing 42a in this case comprises two housing half shells 50a, 52a, which are separably connected to each other along a plane that is oriented parallel to an axial direction 18a and an axial direction 18b which is opposite the axial direction 18a. It is also conceivable, however, for the power tool housing 42a to have two or more pot-shaped housing parts that can be separably connected to each other. The axial direction 18a and the axial direction 18b run along and/or parallelwise in relation to a rotation axis 54a of a hollow shaft 56a of the output unit 48a that is realized as a spindle 40a (FIG. 2). The hollow shaft 56a is provided to drive a working tool 16a in an oscillatory manner, when in a mounted state. Oscillatory driving of the working tool 16a in this case is effected in a manner already known to persons skilled in the art, such as, for example, by means of a peg (not represented in greater detail here) of the transmission unit 46a, which is disposed eccentrically on a drive shaft of the electric motor unit 44a and which, by means of a rocker and an oscillating sleeve (not represented in greater detail here) of the transmission unit 46a, drives the hollow shaft 56a when the portable power tool 38a is in operation. The hollow shaft 56a, realized as a spindle 40a, can therefore be driven in an oscillatory manner. The working tool 16a can be fastened to a tool receiver 58a of the output unit 48a, for the purpose of performing work on workpieces by removal of material. The tool receiver 58a is connected to the hollow shaft 56a in a rotationally fixed manner by means of a positive and/or non-positive connection. It is also conceivable, however, for the tool receiver 58a to be realized so as to be integral with the hollow shaft 56a. A pivoting motion of the hollow shaft 56a can be transmitted to the tool receiver 58a.

FIG. 2 shows a detail view of the tool clamping device 10a when in a tool changing mode, in which an operator can mount the working tool 16a on the tool receiver 58a and/or can alter a position of the working tool 16a relative to the tool receiver 58a, along a circumferential direction 62a. For the purpose of fastening the working tool 16a to the tool receiver 58a in a rotationally fixed manner, the working tool 16a has driving recesses 60a, which are disposed in a circular ring along the circumferential direction 62a, uniformly distributed on the working tool 16a. The working tool 16a has a total of 12 driving recesses 60a (not all represented here), disposed in a uniformly distributed manner in a circular ring along the circumferential direction 62a. It is also conceivable, however, for the working tool 16a to have a number of driving recesses 60a other than 12. The circumferential direction 62a runs in a plane that extends perpendicularly in relation to the axial directions 18a and 18b. The tool receiver 58a has a clamping surface 116 with hump-type protrusions 64a, which corresponds to the driving recesses 60a and which extend from the clamping surface 116 through the driving recesses 60a, along the axial direction 18b, when the working tool 16a is in a mounted state on the tool receiver 58a. The hump-type protrusions 64a in this case are realized as latching cams 66a. The tool receiver 58a has a total of 12 latching cams 66a (not all represented here), which are disposed in a uniformly distributed manner in a circular ring along the circumferential direction 62a. It is also conceivable, however, for the tool receiver 58a to have a number of latching cams 66a other than 12.

Figure 3:
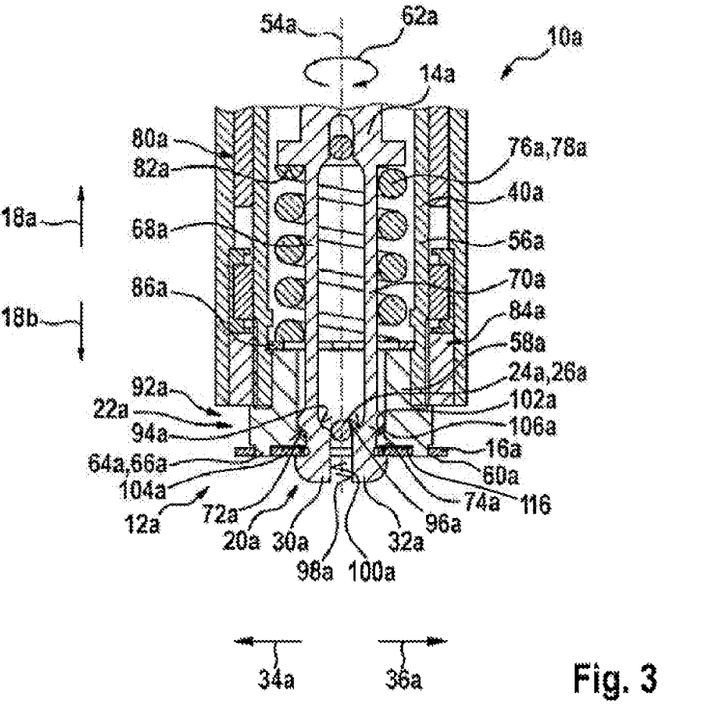
FIG. 3 shows a detail view of the tool clamping device according to the disclosure, in a clamping mode of the clamping unit, in a schematic representation.

The tool clamping device 10a comprises a clamping unit 12a. The clamping unit 12a has a pin-shaped clamping element 14a for chucking the working tool 16a (FIG. 3). The clamping element 14a is disposed in a movable manner in the hollow shaft 56a. The clamping element 14a in this case extends, along the axial direction 18b, through the hollow shaft 56a. When in a mounted state, therefore, the clamping element 14a is disposed in the hollow shaft 56a. Furthermore, the clamping element 14a has two limbs 68a, 70a, which extend at least substantially along the axial direction 18b when the clamping element 14a is in a mounted state. The limbs 68a, 70a are realized so as to be integral with the clamping element 14a. Furthermore, the limbs 68a, 70a have little thickness of material, as viewed along a direction running perpendicularly in relation to the axial direction 18b, in order to enable deflection of the limbs 68a, 70a. Owing to material properties and/or a geometric shape of the limbs 68a, 70a, therefore, the limbs 68a, 70a are disposed on the clamping element 14a so as to be movable relative to each other. The limbs 68a, 70a in this case are disposed in a resilient manner on the clamping element 14a. Furthermore, the limbs 68a, 70a are disposed at a distance relative to each other along the direction running perpendicularly in relation to the axial direction 18a. Owing to their resilient disposition on the clamping element 14a and the relative distance in relation to each other along the direction running perpendicularly in relation to the axial direction 18b, the limbs 68a, 70a can move relative to each other.

Further, the clamping unit 12a has a clamping head 20a, disposed on the clamping element 14a. The clamping head 20a in this case is realized so as to be integral with the clamping element 14a. The clamping head 20a has two partial regions 30a, 32a, which are movable relative to each other. One of the partial regions 30a, 32a, respectively, is disposed on a limb 68a, 70a of the clamping element 14a. The partial regions 30a, 32a of the clamping head 20a in this case are realized, respectively, so as to be integral with one of the limbs 68a, 70a of the clamping element 14a. Consequently, the clamping head 20a is disposed in a resilient manner on the clamping element 14a, by means of the limbs 68a, 70a. In addition, the partial regions 30a, 32a each have a clamping face 72a, 74a, which, when the clamping unit 12a is in a clamping mode, for the purpose of chucking the working tool 16a in the axial direction 18a, bear against at least a partial face of the working tool 16a. The clamping faces 72a, 74a are provided so that, when in the clamping mode, they apply a clamping force to the working tool 16a, in the clamping mode, along the axial direction 18a.

Furthermore, the clamping unit 12a has a spring element 76a, which is provided to apply a spring force to the clamping element 14a, along the axial direction 18b. The spring element 76a in this case is realized as a compression spring 78a. It is also conceivable, however, for the spring element 76a to be constituted by a different spring element, considered appropriate by persons skilled in the art, such as, for example, a tension spring, a disc spring, etc. Further, it is likewise conceivable for the clamping unit 12a to have more than one spring element 76a for applying a spring force to the clamping element 14a. The clamping element 14a, when in a mounted state, extends along the axial direction 18b, through the compression spring 78a. The compression spring 78a is therefore disposed at least around a partial region of the clamping element 14a, along the circumferential direction 62a. The compression spring 78a, when in a mounted state, is supported, by means of an end 80a, on a bearing face 82a of the clamping element 14a. The bearing face 82a in this case is realized in the form of a circular ring. Further, the compression spring 78a is supported, by means of a further end 84a, on a retaining ring 86a disposed on the tool receiver 58a. The retaining ring 86a is provided to bias the compression spring 78a. The retaining ring 86a in this case, when in a mounted state, is disposed in a groove in the hollow shaft 56a. The further end 84a is disposed on a side of the compression spring 78a that is opposite a side of the compression spring 78a on which the compression spring 78a is supported, by means of the end 80a, on the bearing face 82a of the clamping element 14a. The compression spring 78a, therefore, as viewed along the axial direction 18a, is disposed between the bearing face 82a of the clamping element 14a and the retaining ring 86a disposed on the tool receiver 58a. The retaining ring 86a in this case is disposed on a side of the tool receiver 58a that faces in axial direction 18a away from a mounted working tool 16a.

For the purpose of actuating the clamping element 14a, the clamping unit 12a has an operating unit 88a (FIG. 1). The operating unit 88a comprises an operating lever 90a, which is mounted so as to be rotatable about the rotation axis 54a of the hollow shaft 56a. Further, the operating unit 88a has a mechanism (not represented in greater detail here), which is provided to convert a rotary motion of the operating lever 90a about the rotation axis 54a into a translational motion of the clamping element 14a along the axial directions 18a and 18b. The mechanism in this case can be constituted by a transmission, a control cam or other mechanisms, already known to persons skilled in the art, for converting a rotary motion into a translational motion. While the portable power tool 38a is in operation, the operating unit 88a, when in the clamping mode, is decoupled from an oscillating motion of the clamping element 14a, in a manner already known to persons skilled in the art. In the tool changing mode, the operating unit 88a is coupled to the clamping element 14a and/or to the clamping head 20a, in a manner already known to persons skilled in the art, in order to release a clamping force. After the clamping force of the clamping element 14a and/or of the clamping head 20a has been released, the operator can remove the working tool 16a from the tool receiver 58a.

The tool clamping device 10a additionally has a motion conversion unit 22a, which is provided to move the clamping head 20a, in dependence on a motion of the clamping element 14a at least substantially along the axial direction 18b. The clamping head 20a in this case is swiveled, by means of the motion conversion unit 22a, about an axis running perpendicularly in relation to the axial directions 18a and 18b. The clamping head 20a in this case is moved at least substantially along a main motion direction, which runs at least substantially perpendicularly in relation to the axial directions 18a and 18b. The motion conversion unit 22a is realized as an expansion unit 92a, which is provided to move the two partial regions 30a, 32a of the clamping head 20a, which are movable relative to each other, in opposing directions 34a, 36a relative to each other, in an operating mode of the clamping unit 12a. The motion conversion unit 22a in this case has a motion conversion element 24a, which is provided to move the clamping head 20a in a direction differing from the axial directions 18a and 18b, for the purpose of achieving an axial overlap of the clamping head 20a and the working tool 16a, when the clamping unit 12a is in the clamping mode. The motion conversion element 24a is realized as a stud 26a. It is also conceivable, however, for the motion conversion element 24a to be realized as a pin and/or as a slotted pin. Other designs of the motion conversion element 24a, considered appropriate by persons skilled in the art, are likewise conceivable.

For the purpose of mounting the working tool 16a on the tool receiver 58a, the operating lever 90a, starting from a position in which the operating lever 90a bears against the power-tool housing 42a, is moved by the operator in a direction oriented away from the power-tool housing 42a and is therefore rotated about the rotation axis 54a. As a result, the clamping element 14a is moved along the axial direction 18a, in the direction of the tool receiver 58a. The clamping unit 12a is in the tool changing mode. The operator, while maintaining the turning of the operating lever 90a about the rotation axis 54a, can put the working tool 16a on to the tool receiver 58a. It is also conceivable, however, for the operating unit 88a to have a latching device (not represented in greater detail here), which is provided to lock the operating lever 90a in a position, such as, for example, in a position of the operating lever 90a that corresponds to the tool changing mode. The working tool 16a is guided by the operator, with a central insertion opening over the clamping head 20a, until the working tool 16a bears against the tool receiver 58a and the latching cams 66a of the tool receiver 58a are disposed in the driving recesses 60a of the working tool 16a. As a result, when the clamping unit 12a is in the clamping mode, the working tool 16a is secured against turning along the circumferential direction 62a. After a force applied by the operator upon the operating lever 90a has been removed, the operating lever 90a is moved into an initial position, in the direction of the power-tool housing 42a, as a result of a spring force of the compression spring 78a, which acts upon the operating lever 90a via the mechanism for converting the rotary motion of the operating lever 90a into a translational motion of the clamping element 14a. The clamping unit 12a is consequently in the clamping mode.

Upon a motion of the clamping element 14a, along the axial direction 18b, in a direction oriented away from the tool receiver 58a, the two partial regions 30a, 32a of the clamping head 20a are moved on to the motion conversion element 24a, realized as a stud 26a, of the motion conversion unit 22a, realized as an expansion unit 92a. As soon as the partial regions 30a, 32a come into bearing contact with the stud 26a during the motion along the axial direction 18b, respectively one slide face 94a, 96a of the partial regions 30a, 32a slides along an outer face of the stud 26a. The slide faces 94a, 96a have the shape of an arc. Further, the slide faces 94a, 96a are disposed on a side of the partial regions 30a, 32a that faces toward the compression spring 78a. As a result of the motion along the axial direction 18b and the sliding of the slide faces 94a, 96a along the outer face of the stud 26a, the partial regions 30a, 32a are moved in the two mutually opposing directions 34a, 36a, until the stud 26a bears against, respectively, an expansion face 98a, 100a of the partial regions 30a, 32a as a result of the motion of the clamping element 14a between the partial regions 30a, 32a. The stud 26a, as viewed along a direction running perpendicularly in relation to the axial directions 18a and 18b, is disposed between the expansion faces 98a, 100a of the partial regions 30a, 32a, when in the clamping mode. The clamping head 20a is thus expanded by means of the motion conversion element 24a. Following completion of a clamping operation, the clamping faces 72a, 74a of the partial regions 30a, 32a bear against partial faces of the working tool 16a, and apply a clamping force to the working tool 16a, along the axial direction 18a, in the direction of the tool receiver 58a.

In the case of a release operation of the clamping unit 12a, the operator changes the clamping unit 12a from the clamping mode to the tool changing mode. In this case, the operating lever 90a is moved by the operator out of the initial position, in the direction oriented away from the power tool-housing 42a, and rotated about the rotation axis 54a. The clamping element 14a in this case is moved along the axial direction 18a, in the direction of the tool receiver 58a. As a result of the motion of the clamping element 14a along the axial direction 18a, in the direction of the tool receiver 58a, the expansion faces 98a, 100a of the partial regions 30a, 32a slide on the outer face of the stud 26a, until the stud 26a becomes disengaged from the expansion faces 98a, 100a. The partial regions 30a, 32a are moved toward each other as a result of the resilient disposition on the clamping element 14a. For the purpose of assisting the motion of the partial regions 30a, 32a, the motion conversion unit 22a has an inclined face 102a, which is realized so as to correspond, respectively, to an inclined face 104a, 106a of the partial regions 30a, 32a. As soon as the stud 26a has become disengaged from the expansion faces 98a, 100a, the inclined face 102a of the motion conversion unit 22a and the inclined faces 104a, 106a of the partial regions 30a, 32a of the clamping head 20a bear against each other. By means of a combined action of the inclined face 102a of the motion conversion unit 22a and the inclined faces 104a, 106a of the partial regions 30a, 32a, and as a result of the motion of the clamping element 14a along the axial direction 18a, in the direction of the tool receiver 58a, the partial regions 30a, 32a are moved further toward each other. In this case, an axial overlap of the clamping faces 72a, 74a of the partial regions 30a, 32a and of the working tool 16a is removed. The working tool 16a can thus be removed from the tool receiver 58a.

FIGS. 4 to 7 show an alternative exemplary embodiment. Components, features and functions that remain substantially the same are denoted, basically, by the same references. In order to differentiate the exemplary embodiments, the references of the exemplary embodiments have the suffix letters a and b. The description that follows is limited substantially to the differences in relation to the first exemplary embodiment in FIGS. 1 to 3, and reference may be made to the description of the first exemplary embodiment in FIGS. 1 to 3 in respect of components, features and functions that remain the same.

Figure 4:
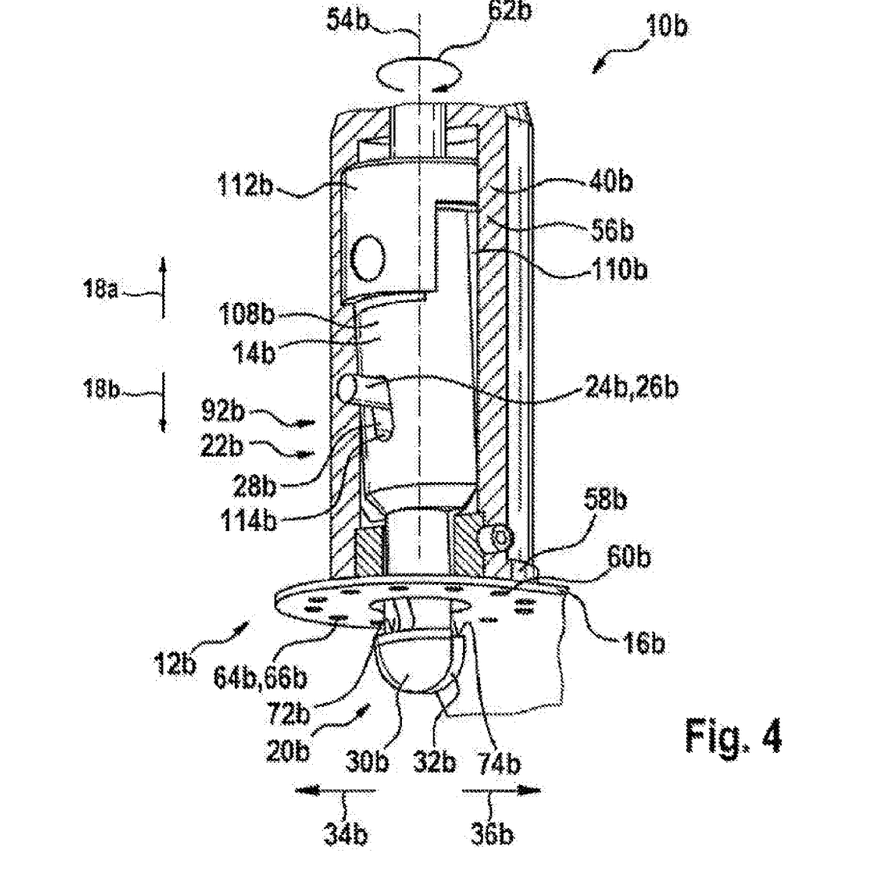
FIG. 4 shows a detail view of an alternative tool clamping device according to the disclosure, in a tool changing mode of a clamping unit of the alternative tool clamping device according to the disclosure, in a schematic representation.

FIG. 4 shows a detail view of a tool clamping device 10b when a clamping unit 12b of the tool clamping device 10b is in a tool changing mode. The tool clamping device 10b is disposed in a portable power tool (not represented in greater detail here), which has a structure similar to that of the portable power tool 42a from FIG. 1. The clamping unit 12b has a pin-shaped clamping element 14b for chucking a working tool 16b in an axial direction 18b, and has a clamping head 20b disposed on the clamping element 14b. Furthermore, the tool clamping device 10b has a motion conversion unit 22b, which is provided to move the clamping head 20b, in dependence on a motion of the clamping element 14b at least substantially along the axial direction 18b, in at least one direction differing from the axial direction 18b.

The clamping element 14b comprises two partial regions 108b, 110b, which are movable relative to each other. The partial regions 108b, 110b of the clamping element 14b are disposed, so as to be swivellable about an axis running perpendicularly in relation to the axial direction 18b, in a spindle 40b of the portable power tool that is realized as a hollow shaft 56b. In addition, the partial regions 108b, 110b are mounted so as to be movable in the hollow shaft 56b, along the axial direction 18b. The clamping element 14b is disposed in a movable manner on a transmission element 112b of the clamping unit 12b. The transmission element 112b is provided to transmit a motion of an operating unit (not represented in greater detail here) of the clamping unit 12*b* to the clamping element 14*b*. The clamping head 20*b* likewise has two partial regions 30*b*, 32*b* that are movable relative to each other. The partial regions 30*b*, 32*b* of the clamping head 20*b* are realized, respectively, so as to be integral with one of the partial regions 108*b*, 110*b* of the clamping element 14*b*. Further, the partial regions 30*b*, 32*b* of the clamping head 20*b* are disposed, respectively, on the respective partial region 108*b*, 110*b* of the clamping element 14*b*. In this case, the partial regions 30*b*, 32*b* of the clamping head 20*b* have an eccentricity relative to a longitudinal axis of the respective partial region 108*b*, 110*b* of the clamping element 14*b* that, at least in one operating state, runs at least substantially parallelwise in relation to the axial direction 18*b*.

Furthermore, the motion conversion unit 22*b* comprises a motion conversion element 24*b*, which is provided to move the clamping head 20*b* in at least one direction differing from the axial direction 18*b*, for the purpose of achieving an axial overlap of the clamping head 20*b* and the working tool 16*b*, at least when the clamping unit 12*b* is in a clamping mode. The motion conversion element 24*b* is realized as a stud 26*b*. Further, the motion conversion unit 22*b* comprises at least one cam member 28*b*, in which the motion conversion element 24*b* partially engages. The motion conversion unit 22*b* is thus constituted by a cam mechanism. The cam mechanism in this case is realized as an expansion unit 92*b*, which is provided to move the two partial regions 30*b*, 32*ab* of the clamping head 20*b*, which are movable relative to each other, in opposing directions 34*b*, 36*b* relative to each other, in at least one operating mode of the clamping unit 12*a*.

The cam member 28*b* is disposed on the clamping element 14*b*. The partial regions 108*b*, 110*b* of the clamping element 14*b* each comprise a cam member 28*b* (only one cam member is represented in the figures). The cam members 28*b* are realized as gate-type slots 114*b* (only one slot represented in the figures) in the partial regions 108*b*, 110*b* of the clamping element 14*b*. It is also conceivable, however, for the cam members 28*b* to be designed in a different manner, considered appropriate by persons skilled in the art. The slots 114*b* are provided to define a motion of the respective partial region 108*b*, 110*b* in dependence on a motion of the clamping element 14*b* along the axial direction 18*b*, by means of a combined action with the motion conversion element 24*b*. The motion conversion element 24*b*, when in a mounted state, extends along a direction running perpendicularly in relation to the axial direction 18*b*, through the slots 114*b* of the partial regions 108*b*, 110*b*. The motion conversion element 24*b* is connected to the hollow shaft 56*b* in a fixed manner.

Figure 5:
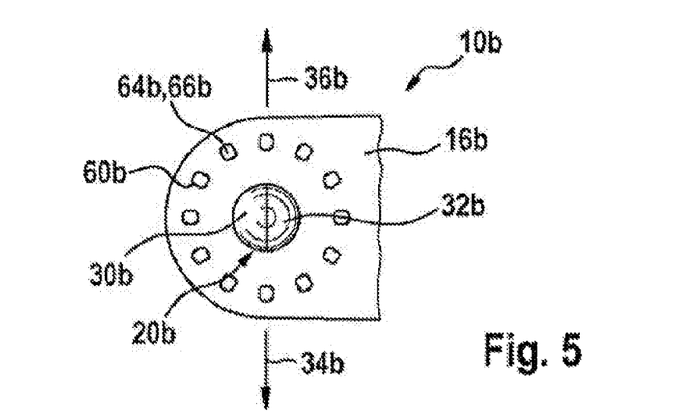
FIG. 5 shows a detail view of a clamping head of a clamping unit of the alternative tool clamping device according to the disclosure, in a tool changing mode of the clamping unit, in a schematic representation.

When the working tool 16*b* is being mounted, the clamping unit 12*b* is in a tool changing mode. In this case, the partial regions 108*b*, 110*b* of the clamping element 14*b* are swiveled relative to each other, because of the motion conversion unit 22*b*. Consequently, longitudinal axes of the partial regions 108*b*, 110*b* are offset at an angle relative to the axial direction 18*b*. The partial regions 30*b*, 32*b* of the clamping head 20*b* are disposed concentrically in relation to the axial direction 18*b*, owing to the eccentric disposition on the partial regions 108*b*, 110*b* of the clamping element 14*b*, in the region of clamping faces 72*b*, 74*b* of the partial regions 30*b*, 32*b* (FIG. 5). An operator can thus attach the working tool 16*b* to a tool receiver 58*b* of the portable power tool. The working tool 16*b* in this case is guided with a central insertion opening over the clamping head 20*b*, until the working tool 16*b* bears against the tool receiver 58*b* and protrusions 64*b* of the tool receiver 58*b* are disposed in driving recesses 60*b* of the working tool 16*b*.

Figure 6:
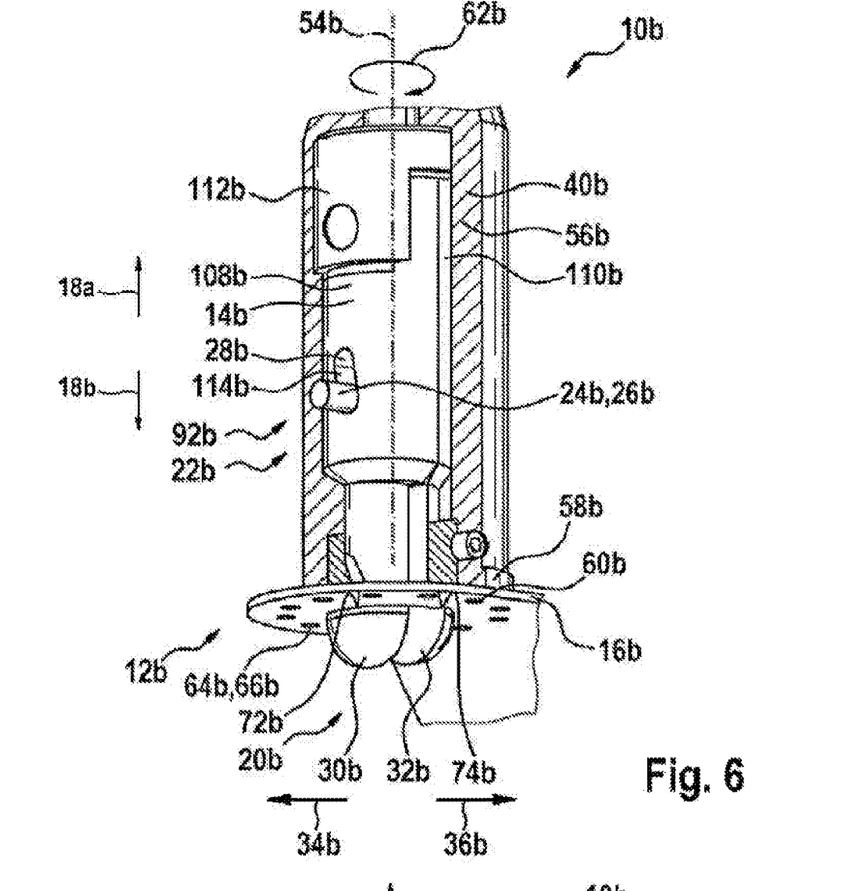
FIG. 6 shows a detail view of the alternative tool clamping device according to the disclosure from FIG. 4, in a clamping mode of the clamping unit, in a schematic representation.

FIG. 6 shows the clamping unit 12*b* in a clamping mode. As the clamping unit 12*b* is being changed from the tool changing mode to the clamping mode, the partial regions 108*b*, 110*b* of the clamping element 14*b* are swiveled relative to each other during a motion of the clamping element 14*b* along the axial direction 18*b*, as a result of a combined action of the motion conversion element 24*b* and the cam members 28*b*. Upon a motion of the clamping element 14*b* in a direction oriented away from the tool receiver 58*b*, the partial regions 108*b*, 110*b* are swiveled toward each other, because of a geometry of the cam members 28*b*. In the clamping mode, the longitudinal axes of the partial regions 108*b*, 110*b* are aligned parallelwise in relation to the axial direction 18*b*. Consequently, the partial regions 108*b*, 110*b* overlap at least substantially completely along a direction running perpendicularly in relation to the axial direction 18*b*. In this case, the outer edges of the partial regions 108*b*, 110*b* are each in flush alignment with each other along the direction running perpendicularly in relation to the axial direction 18*b*.

Figure 7:
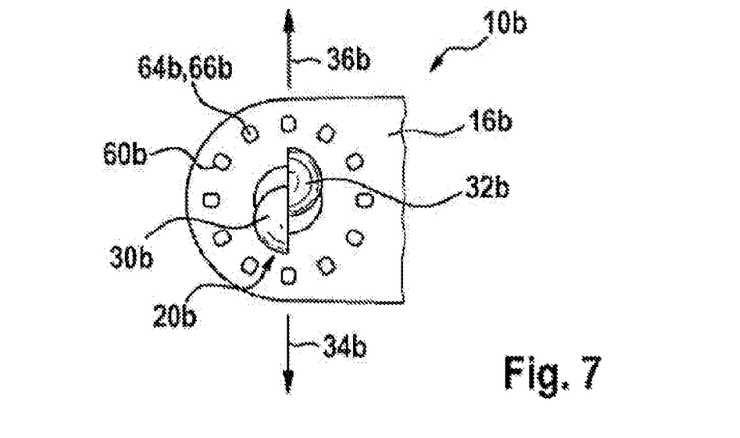
FIG. 7 shows a detail view of the clamping head of the clamping unit of the alternative tool clamping device according to the disclosure, in a clamping mode of the clamping unit, in a schematic representation.

Upon a swivel motion of the partial regions 108*b*, 110*b* of the clamping element 14*b*, the partial regions 30*b*, 32*b* of the clamping head 20*b* are moved relative to each other in opposing directions 34*b*, 36*b*. The partial regions 30*b*, 32*b* of the clamping head 20*b* are moved substantially along a main motion component, which is aligned perpendicularly in relation to the axial direction 18*b*. As a result of the motion of the partial regions 30*b*, 32*b* of the clamping head 20*b*, the clamping faces 72*b*, 74*b* of the partial regions 30*b*, 32*b* are placed against the working tool 16*b*. Consequently, in the clamping mode, a clamping force is transmitted, along the axial direction 18*b*, to the working tool 16*b*. The partial regions 30*b*, 32*b* of the clamping head 20*b* are disposed with an offset relative to each other, owing to the eccentric disposition on the partial regions 108*b*, 110*b* in the clamping mode (FIG. 7).

The invention claimed is:

1. A portable power tool, comprising:
 a portable housing;
 a motor enclosed in the housing;
 a hollow shaft configured to be driven to oscillate about an oscillation axis by the motor, the hollow shaft having a tool receiver disposed at a first end thereof, the tool receiver including a clamping surface that is configured to receive a working tool, the clamping surface being arranged facing at least partially in a first axial direction that is parallel to the oscillation axis;
 at least one clamping unit having (i) at least one pin-shaped clamping element that extends through the hollow shaft and movable with respect to the hollow shaft in the first axial direction and in a second axial direction opposite the first axial direction and (ii) at least one clamping head disposed on the clamping element, the clamping head having a clamping face that is arranged facing in the second axial direction, the clamping element extending from the hollow shaft to position the clamping head with the clamping face facing the clamping surface, wherein movement of the clamping element with respect to the hollow shaft in the second axial direction moves the clamping face of the clamping head toward the clamping surface of the work receiver so as to press the working tool against the clamping surface with a clamping force, and
 at least one motion conversion unit that is configured to move the clamping head in at least one direction differing from the second axial direction when the clamping head is moved with the clamping element in the second axial direction, wherein the motion conversion unit has at least one motion conversion element configured to move the clamping head in at least one direction differing from the axial direction so as to achieve an axial overlap of the clamping head and the working tool at least when the clamping unit is in a clamping mode.

2. The portable power tool as claimed in claim 1, wherein the motion conversion element is realized as a stud.

3. The portable power tool as claimed in claim 1, wherein the clamping head is disposed in a resilient manner on the clamping element.

4. The portable power tool as claimed in claim 1, wherein the motion conversion unit has at least one cam member configured to engage the motion conversion element.

5. The portable power tool as claimed in claim 4, wherein the cam member is disposed on the clamping element.

6. The portable power tool as claimed in claim 4, wherein the at least one cam member of the motion conversion unit is configured to partially engage the motion conversion element.

7. The portable power tool as claimed in claim 1, wherein the clamping head has at least two partial regions that are movable relative to each other.

8. The portable power tool as claimed in claim 1, wherein the motion conversion unit is realized as an expansion unit configured to move at least two partial regions of the clamping head, the two partial regions being movable relative to each other in oppositely oriented directions relative to each other in at least one operating mode of the clamping unit.

9. The portable power tool as claimed in claim 1, wherein the clamping head is realized so as to be integral with the clamping element.

10. The portable power tool as claimed in claim 1, wherein the clamping head has a first and a second partial region that are movable relative to each other, wherein the motion conversion element comprises a first cam provided on the first partial region, a second cam provided on the second partial region, and a stud positioned in the hollow shaft in engagement with the first cam and the second cam, and wherein movement of the clamping element in the first axial direction moves the first cam and the second cam with respect to the stud, the movement of the first cam and the second cam with respect to the stud causing the partial regions to move with respect to each other in a direction transverse to the first and second axial directions.

11. The portable power tool as claimed in claim 10, wherein the first cam and the second cam each comprise a slot through which the stud extends.

12. The portable power tool as claimed in claim 10, wherein the stud is fixedly attached to the hollow shaft.

13. A portable power tool, comprising:
a portable housing;
a motor enclosed in the housing;
a hollow shaft configured to be driven to oscillate about an oscillation axis by the motor, the hollow shaft having a tool receiver disposed at a first end thereof, the tool receiver including a clamping surface that is configured to receive a working tool, the clamping surface being arranged facing at least partially in a first axial direction that is parallel to the oscillation axis;

at least one clamping unit having (i) at least one pin-shaped clamping element that extends through the hollow shaft and movable with respect to the hollow shaft in the first axial direction and in a second axial direction opposite the first axial direction and (ii) at least one clamping head disposed on the clamping element, the clamping head having a clamping face that is arranged facing in the second axial direction, the clamping element extending from the hollow shaft to position the clamping head with the clamping face facing the clamping surface, wherein movement of the clamping element with respect to the hollow shaft in the second axial direction to brings the clamping face of the clamping head toward the clamping surface of the work receiver so as to press the working tool against the clamping surface with a clamping force; and at least one motion conversion unit on the tool receiver,
wherein the clamping head has at least two partial regions that are movable relative to each other in directions transverse to the first and second axial directions, each of the partial regions including an inclined surface that faces in the second axial direction, wherein the motion conversion unit comprises an inclined face on the tool receiver that faces in the first axial direction, and wherein movement of the clamping element in the first axial direction moves the inclined face of the motion conversion unit into engagement with the inclined surfaces on the partial regions of the clamping head, the engagement between the inclined face and the inclined surfaces causing the partial regions to move with respect to each other in a direction transverse to the first and second axial directions.

14. A portable power tool, comprising:
a portable housing;
a motor enclosed in the housing;
a hollow shaft configured to be driven to oscillate about an oscillation axis by the motor, the hollow shaft having a tool receiver disposed at a first end thereof, the tool receiver including a clamping surface that is configured to receive a working tool, the clamping surface being arranged facing at least partially in a first axial direction that is parallel to the oscillation axis;

at least one clamping unit having (i) at least one pin-shaped clamping element that extends through the hollow shaft and movable with respect to the hollow shaft in the first axial direction and in a second axial direction opposite the first axial direction and (ii) at least one clamping head disposed on the clamping element, the clamping head having a clamping face that is arranged facing in the second axial direction, the clamping element extending from the hollow shaft to position the clamping head with the clamping face facing the clamping surface, wherein movement of the clamping element with respect to the hollow shaft in the second axial direction moves the clamping face of the clamping head toward the clamping surface of the work receiver so as to press the working tool against the clamping surface with a clamping force, and at least one motion conversion unit that is configured to move the clamping head in at least one direction differing from the second axial direction when the clamping head is moved with the clamping element in the second axial direction, wherein the clamping head has at least two partial regions that are movable relative to each other.

* * * * *

UNITED STATES PATENT AND TRADEMARK OFFICE
CERTIFICATE OF CORRECTION

PATENT NO. : 9,486,887 B2
APPLICATION NO. : 13/981512
DATED : November 8, 2016
INVENTOR(S) : Fankhauser et al.

Page 1 of 1

It is certified that error appears in the above-identified patent and that said Letters Patent is hereby corrected as shown below:

In the Claims

In Column 14, Lines 1-5, Lines 11-15 of Claim 13 should read:

at least one clamping unit having (i) at least one pin-
shaped clamping element that extends through the
hollow shaft and is movable with respect to the hollow
shaft in the first axial direction and in a second axial
direction opposite the first axial direction and (ii) at In Column 14, Lines 11-16, Lines 21-26 of Claim 13 should read:

facing the clamping surface, wherein movement of the
clamping element with respect to the hollow shaft in
the second axial direction brings the clamping face
of the clamping head toward the clamping surface of
the work receiver so as to press the working tool against
the clamping surface with a clamping force; and Signed and Sealed this
Seventh Day of March, 2017

Michelle K. Lee
*Director of the United States Patent and Trademark Office*